US010168198B2

(12) United States Patent
Cobianu et al.

(10) Patent No.: US 10,168,198 B2
(45) Date of Patent: Jan. 1, 2019

(54) BULK ACOUSTIC WAVE (BAW) SENSORS FOR LIQUID LEVEL MEASUREMENTS

(71) Applicant: HONEYWELL INTERNATIONAL INC., Morristown, NJ (US)

(72) Inventors: Cornel Cobianu, Bucharest (RO); Ion Georgescu, Bucharest (RO); Cazimir Gabriel Bostan, Bucharest (RO)

(73) Assignee: Honeywell International Inc., Morristown, NJ (US)

( * ) Notice: Subject to any disclaimer, the term of this patent is extended or adjusted under 35 U.S.C. 154(b) by 571 days.

(21) Appl. No.: 14/577,487

(22) Filed: Dec. 19, 2014

(65) Prior Publication Data

US 2015/0177045 A1 Jun. 25, 2015

(30) Foreign Application Priority Data

Dec. 24, 2013 (EP) .................................... 13199529

(51) Int. Cl.

*G01F 23/296* (2006.01)
*G01N 29/036* (2006.01)
*G01N 29/22* (2006.01)
*G01N 29/44* (2006.01)

(52) U.S. Cl.

CPC ........ *G01F 23/296* (2013.01); *G01F 23/2966* (2013.01); *G01F 23/2968* (2013.01); *G01N 29/036* (2013.01); *G01N 29/222* (2013.01); *G01N 29/4427* (2013.01); *G01N 2291/02818* (2013.01); *G01N 2291/02836* (2013.01); *G01N 2291/0422* (2013.01); *G01N 2291/0427* (2013.01)

(58) Field of Classification Search

CPC ............... G01F 23/296; G01F 23/2966; G01F 23/2968; G01N 29/02; G01N 29/036; G01N 29/222; G01N 29/4427; G01N 2291/02818; G01N 2291/02836; G01N 2291/0422; G01N 2291/0427

USPC ........................................................ 367/140

See application file for complete search history.

(56) References Cited

U.S. PATENT DOCUMENTS 5,211,054 A * 5/1993 Muramatsu ............ G01N 11/16
73/54.25
6,455,316 B1 * 9/2002 Turner .............. B01F 15/00207
374/E13.001
6,455,319 B1 * 9/2002 Lewis .................. G01N 27/126
422/68.1

(Continued)

FOREIGN PATENT DOCUMENTS

WO WO-2006084263 A2 * 8/2006 ......... G01F 23/2966

*Primary Examiner* — Isam A Alsomiri
*Assistant Examiner* — Amie M Ndure
(74) *Attorney, Agent, or Firm* — Jetter & Associates, P.A.

(57) ABSTRACT

A method for sensing at least one level parameter of at least one liquid in a tank. At least one bulk acoustic wave (BAW) sensor is positioned inside the tank. Electrodes of the BAW sensor are at least switchably connected to a positive feedback loop across an amplifier to provide an electronic oscillator. At least one acoustic viscosity measurement is determined from an output of the electronic oscillator, wherein the output of the electronic oscillator is different when the BAW sensor contacts the liquid as compared to when the BAW sensor contacts air. The level parameter is determined from the acoustic viscosity measurement.

13 Claims, 5 Drawing Sheets

(56) References Cited

U.S. PATENT DOCUMENTS 6,787,112 B1 * 9/2004 Turner .............. B01F 15/00201 374/E13.001
6,864,092 B1 * 3/2005 Turner .............. B01F 15/00201 374/E13.001
6,890,492 B1 * 5/2005 Turner .............. B01F 15/00201 366/244
6,924,149 B2 * 8/2005 Turner .............. B01F 15/00201 374/E13.001
7,103,460 B1 * 9/2006 Breed ................. B60C 23/0408 701/29.1
7,148,611 B1 12/2006 Liu
7,450,618 B2 * 11/2008 Dantus ............... G01B 9/02014 250/281
8,024,133 B2 * 9/2011 Homer ................. G01N 27/121 702/24
8,342,027 B2 * 1/2013 Walton ................. G01N 29/022 73/584
8,450,904 B2 * 5/2013 Iwamoto .................. H03H 3/08 310/313 R
8,454,819 B2 * 6/2013 Neethirajan ......... G01N 33/004 204/415
2002/0017126 A1 * 2/2002 DiMeo, Jr. ............. G01N 21/59 73/31.05
2002/0192117 A1 * 12/2002 Lewis .................. G01N 27/126 422/82.05
2003/0201694 A1 * 10/2003 Lu ...................... H03H 9/02976 310/313 A
2004/0040841 A1 * 3/2004 Gonzalez-Martin ......................... G01N 27/126 204/406
2005/0192727 A1 * 9/2005 Shostak .................. B60C 11/24 701/37
2006/0085049 A1 * 4/2006 Cory .................... A61B 5/0536 607/48
2006/0283252 A1 * 12/2006 Liu ...................... G01N 29/022 73/649
2007/0272209 A1 11/2007 Matsiev et al.
2009/0214762 A1 * 8/2009 Lewis ................ G01N 33/0031 427/58
2009/0216467 A1 * 8/2009 Andle .................... G01N 9/002 702/54
2010/0317420 A1 * 12/2010 Hoffberg ............ G06Q 30/0207 463/1
2011/0004513 A1 * 1/2011 Hoffberg ............ G06Q 30/0207 705/14.1

* cited by examiner

BULK ACOUSTIC WAVE (BAW) SENSORS FOR LIQUID LEVEL MEASUREMENTS

CROSS REFERENCE TO RELATED APPLICATIONS

This application claims the benefit of EP Application Serial No. 13199529.2 entitled "BULK ACOUSTIC WAVE (BAW) SENSORS FOR LIQUID LEVEL MEASUREMENTS", filed Dec. 24, 2013, which is herein incorporated by reference in its entirety.

FIELD

Disclosed embodiments relate to systems including acoustic wave sensors for sensing liquid levels.

BACKGROUND

On-line measurement of the level of liquids or powders in storage tanks is extensively used for process control in the chemical, petrochemical and medical industry, as well as in custody transfer, marine and transportation operations. For this purpose, there are a variety of mechanical, electrical, magnetic methods and instruments (transmitters) for detecting point and continuous level for liquids and powders. For example, there are continuous level transmitters including non-contact radar, guided wave radar (GWR), non-contact ultrasonics, differential pressure, capacitive, magnetostrictive, displacers, and laser.

Continuous level measurements can be made either by a contact method (e.g. GWR, differential pressure, capacitive, displacers), where the transmitter is immersed in the liquid, or by keeping the transmitter outside the liquid (non-contact method), such as in the case of non-contact radar, ultrasonics, and laser. Each of these methods has both advantages and limitations, and in practice, the selection of the most appropriate method for a particular situation is made by taking into consideration the specific application requirements, such as the chemical nature of liquid, process conditions, etc. For many applications where an actuation decision is taken when the liquid (or powder) level is too high or too low, point level measurement by using switches is generally used, such as using a vibrating fork, capacitive, float and displacer switches.

A more complex problem is the detection of both the level and interface between two immiscible liquids, such as in the case of oil and water, where oil having lower gravimetric density will remain on the upper side of the interface, while water having a higher gravimetric density will occupy the bottom side of the interface. For such a case, contact methods are generally used (e.g., GWR, differential pressure), where both the hardware and software algorithms are more complex (compared to non-contact methods) such as in the case of differential pressure method, where two pressure sensors are used, or complex software is used, in order to discriminate between upper level, the interface, the bottom side or parasitic reflections, such as in the case of the GWR method. In addition, to detect an interface between two liquids, a number of conditions need to be fulfilled, including the dielectric constant difference between the two media should generally be at least equal to 10. Detection of more than one interface is even more challenging, if not impossible, for known contact methods.

SUMMARY

This Summary is provided to introduce a brief selection of disclosed concepts in a simplified form that are further described below in the Detailed Description including the drawings provided. This Summary is not intended to limit the claimed subject matter's scope.

Disclosed embodiments recognize although acoustic wave devices such as surface acoustic wave (SAW) devices and SAW-like devices may be used for liquid level sensing, they experience damping in liquid, and are thus limited to only the binary function of a liquid presence sensor. Disclosed embodiments are instead directed to Bulk Acoustic Wave (BAW) sensors for level monitoring of liquids which has been recognized by the Inventors provide a contact-method for detecting fluid level parameters including point level, quasi-continuous level, and multiple interfaces in the case of two or more different immiscible liquids in a given tank.

Unlike SAW or SAW-like devices, shear vibrations of BAW devices are travelling both in the bulk and along the surface of the piezoelectric crystal substrate, and are not easily damped by the loading liquid, which enables additional measurements to be realized, including the measurement of the quasi-continuous level, and multiple interfaces in the case of different immiscible liquids together in a given tank. The BAW device can comprise a shear horizontal acoustic plate mode (SHAPM) device or a thickness shear mode (TSM) device.

BRIEF DESCRIPTION OF THE DRAWINGS

FIGS. 2A-B are simplified depictions of example BAW devices including an example SHAPM device in FIG. 2A, while FIG. 2B depicts an example TSM device.

DETAILED DESCRIPTION

Figure 1:
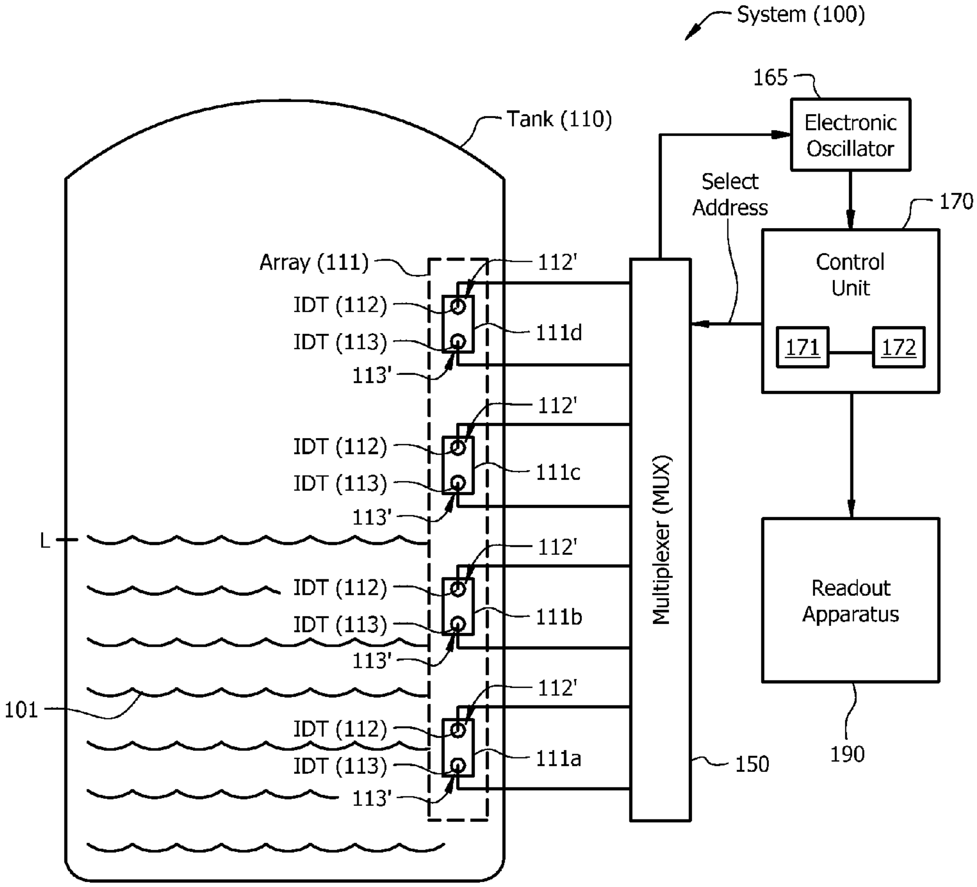
FIG. 1 is a functional block diagram depiction of an example system for sensing at least one level parameter of at least one liquid in a tank including a plurality of BAW sensors inside the tank, according to an example embodiment.

Disclosed embodiments are described with reference to the attached figures, wherein like reference numerals are used throughout the figures to designate similar or equivalent elements. The figures are not drawn to scale and they are provided merely to illustrate certain disclosed aspects. Several disclosed aspects are described below with reference to example applications for illustration. It should be understood that numerous specific details, relationships, and methods are set forth to provide a full understanding of the disclosed embodiments.

One having ordinary skill in the relevant art, however, will readily recognize that the subject matter disclosed herein can be practiced without one or more of the specific details or with other methods. In other instances, well-known structures or operations are not shown in detail to avoid obscuring certain aspects. This Disclosure is not limited by the illustrated ordering of acts or events, as some acts may occur in different orders and/or concurrently with other acts or events. Furthermore, not all illustrated acts or events are required to implement a methodology in accordance with the embodiments disclosed herein.

Also, the terms "coupled to" or "couples with" (and the like such as "connected to") as used herein in the electrical context without further qualification are intended to describe either an indirect or direct electrical connection. Thus, if a first device "couples" to a second device, that connection can be through a direct electrical connection where there are only parasitics in the pathway, or through an indirect electrical connection via intervening items including other devices and connections. For indirect coupling, the intervening item generally does not modify the information of a signal but may adjust its current level, voltage level, and/or power level.

FIG. 1 is a functional block diagram depiction of an example system 100 for sensing at least one level parameter of at least one liquid 101 in a tank 110 including a plurality of BAW sensors 111*a*, 111*b*, 111*c* and 111*d* (BAW sensor array 111) inside the tank, according to an example embodiment. Although shown in FIG. 1 is SHAPM devices, the BAW sensors in BAW sensor array 111 can be SHAPM devices or TSM devices. System 100 is shown as a fully wire connected system. As known in the acoustic sensing arts, acoustic sensing functions by monitoring a change in oscillation frequency of an electronic oscillator circuit when the acoustic device in a feedback loop across the oscillator responds to an input stimulus. An electronic oscillator is thus a closed loop device which may be contrasted with a mechanical oscillator which operates in an open loop nature, such as a tuning fork stimulated by a frequency generator. Although a wireless or partially wireless system is possible for disclosed systems, the operation of wireless acoustic sensors immersed in liquid will generally impose implementation challenges as the antenna of the wireless acoustic sensors would be immersed in the liquid.

Disclosed embodiments solve the problem of complexity in the sensor electronics and in the signal processing. By forming an electronic oscillator by coupling the respective electrodes of the claimed BAW sensor across the feedback loop of the amplifier, the need for a frequency generator required in known level sensing systems to electrically stimulate the sensor is eliminated, and the level parameter can be determined from the acoustic viscosity measurement without any dependence on a frequency generator source applied to the level sensor.

The liquid 101 is shown in the tank 110 filled to a level L. BAW sensor array 111 includes BAW sensors 111*a*, 111*b*, 111*c* and 111*d* shown stacked vertically along a vertical wall of the tank 110. Each BAW sensor 111*a-d* has an input interdigitated transducer (IDT) 112 and output IDT 113 that represents the electrode configuration for SHAPM devices. For TSM devices, as noted below, they in contrast have a relatively simple pair of electrodes, with one electrode typically on the top side of the substrate and one electrode on the bottom side of the substrate. The respective electrodes for the IDTs 112 and 113 (or a first electrode (e.g., top) and a second (e.g. bottom) electrode for TSM devices) can comprise aluminum (Al) or an Al alloy, and their thickness can be set to roughly (1/100) to 1/20 of their line pitch, with an electrode thickness generally below 1 μm, such as between 10 nm and 100 nm. The vertical spacing between BAW sensors 111*a*, 111*b*, 111*c* and 111*d* is typically a constant distance, although this is not a requirement since only the absolute vertical position (e.g., relative to the bottom of the tank 110) for each BAW sensor is needed by sensing system 100 to provide liquid level calculations.

The system 100 includes a readout apparatus (circuit) 190, a multiplexer (MUX) 150, and a control unit 170. Although not shown, there will generally be an analog to digital converter (ADC) and a filter between the readout apparatus 190 and control unit 170. Control unit 170 includes a processor 171 (e.g., a digital signal processor (DSP) or microcontroller unit (MCU)) and an associated memory 172 (typically a non-volatile memory) which can store information including programs/algorithms and a unique digital address for each the BAW sensors 111*a*, 111*b*, 111*c* and 111*d* in sensing array 111, and other information such as calibration coefficients related to BAW sensor operation at different temperatures, based on information provided by temperature sensors provided in system 100 (not shown).

For $2^n$ BAW sensors, there will be n address lines (e.g., 4 lines for 16 BAW sensors). Inputs to the MUX 150 are coupled to one of the electrodes of the respective input IDTs 113 and output IDTs 112 of the BAW sensors 111*a*, 111*b*, 111*c* and 111*d* in the BAW sensor array 111. The referential numbers 111*a-d* in FIG. 1 are not used to represent/limit the number of the BAW sensors in the BAW sensor array 111. Those skilled in the art can deduce sensor arrays of other layout structures and sensor numbers according to the description provided herein.

The control unit 170 including processor 171 controls the MUX 150 by providing a binary select address for selecting a target BAW sensor from the BAW sensors 111*a*-111*d* of the BAW sensor array 111 to read. The readout apparatus 190 is connected to the control unit 170, which will receive information from the output of the resulting electronic oscillator 165 which can include an amplifier (not shown in FIG. 1, but see FIG. 3A described below showing amplifier 140 having a BAW sensor embodied as a SHAPM device connected in a positive feedback loop). For example any one of the BAW sensors 111*a*-111*d* of the BAW sensor array 111 can be connected via MUX 150 into the positive feedback loop of an amplifier to provide the electronic oscillator 165, with electrode 113' of the input IDT 113 connected to the output of the amplifier, and the one of the electrodes 112' of the output IDT 112 connected to the input of amplifier. Such an electronic oscillator 165 can be realized from simple circuitry such as a single transistor, or from more complex electronic circuitry including a plurality of circuit elements (transistors, resistors and/or capacitors and inductors). As known in the electronic arts, and as used herein, an electronic oscillator is an electronic circuit that produces a repetitive, oscillating electronic signal, often a sine wave or a square wave when loaded, described herein loaded with a BAW sensor, such as an amplifier loaded with a BAW sensor in a positive feedback loop of the amplifier.

The value of the oscillation frequency of the electronic oscillator 165 for each BAW sensor from the BAW sensor array 111, "facilitated" by the MUX 150 is sent to the control unit 170. After signal processing according to level/interface measurements described below, the level/interface value is sent to the readout apparatus 190, such as to allow plant personnel, such as an operator, technician, or engineer to view the level/interface information. In operation, the BAW sensors 111*a*, 111*b*, 111*c* and 111*d* in the BAW sensor array 111 may be read out one at a time as controlled by control unit 170 in conjunction with MUX 150.

Since the BAW sensors 111*a*-111*d* (either SHAPM or TSM) are "labeled" with a unique digital address, the MUX 150 allows interrogating the BAW sensors 111*a*-111*d* individually (one at a time). Thus, in response to the interrogation (address select) signal from control unit 170, a particular BAW sensor can become coupled across the feedback loop of an amplifier provided by the electronic oscillator 165 to change the resonant frequency of the resulting electronic oscillator 165, thus enabling the processor of control unit 170 to determine a local value (corresponding to a height location of the particular BAW sensor) of acoustic viscosity via a change in resonant frequency of the electronic oscillator 165 using a stored calibration curve relating a change in resonant frequency for the electronic oscillator 165 to acoustic viscosity. Thus, for system 100 shown in FIG. 1, the local acoustic viscosity reported can be related to the frequency shift of the electronic oscillator 165 with the particular BAW sensor 111*a*-111*d* within the positive feedback loop of the amplifier provided by electronic oscillator 165.

BAW devices are recognized as being able to detect liquids' properties (e.g., density and viscosity, electro-acoustic interactions due to their shear waves). As noted above example BAW sensors include SHAPM devices and TSM devices. Regarding BAW devices electrodes, SHAPM devices have a pair of IDTs as described above, while TSM devices have a relatively simple (typically circular) first and second electrodes (one electrode on the top side of the substrate, and one electrode the bottom side) described below relative to FIG. 2B.

The BAW devices described relative to FIGS. 2A and 2B below are able to detect liquid's properties (e.g., density and viscosity, electro-acoustic interactions) due to their shear waves during operation. With SHAPM and TSM devices, the Inventors have recognized one can measure the local acoustic viscosity of liquid for level/interface detection, which is believed to be a new application for BAW sensors.

BAW sensors measure the acoustic density (the product of density and viscosity), which as disclosed herein can be used to discriminate different liquid phases between them, or to indicate that the BAW sensor is exposed to a gas, typically air. As an example, the acoustic viscosity of air is almost equal to zero, while the acoustic viscosity of water is 2.15 ($g/cm^3$) Cp, and that of lubricating oil is about 735 ($g/cm^3$) Cp. This data evidences that BAW devices, as disclosed herein, can be used as switches in point level detection, indicating "overfilled" or "empty" liquid state in tanks for different applications (see FIGS. 3C and 3D described below), or even an inexpensive liquid spectrometer discriminating between different types of liquids (water, oil, etc).

Figure 2A:
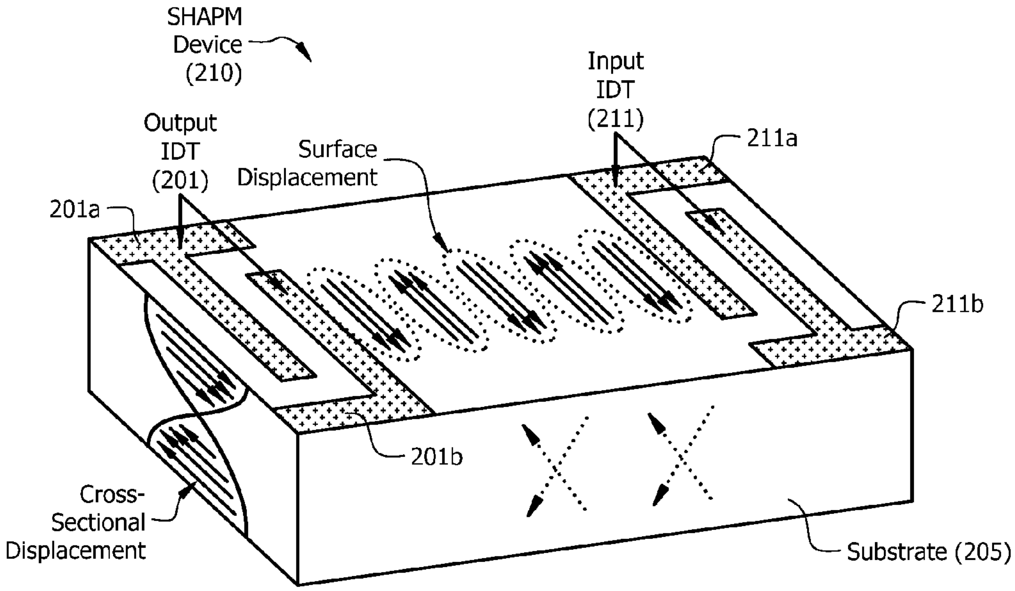

FIG. 2A depicts an example SHAPM device 210. SHAPM device 210 includes a piezoelectric crystal substrate 205 which can comprise quartz, lithium tantalate, lithium niobate, or other piezoelectric material. SHAPM device 210 includes an input IDT 211 including electrodes 211*a*, 211*b* interdigitated with respect to one another used to generate and launch acoustic shear waves inside the piezoelectric crystal substrate 205 responsive to a received alternating current (AC) electric signal coming from the output of a suitable signal source, such as an amplifier.

In typical operation, the input AC signal applied to IDT 211 has a frequency of about 5 MHz, and its voltage level is given by the output of the amplifier or other signal source with optional voltage limiting. The electrodes 201*a*, 201*b* of output IDT 201 capture and convert the received shearwaves into electrical signals. For SHAPM device 210, during operation the acoustic energy is distributed on standing waves inside entire piezoelectric crystal substrate 205 as shown in FIG. 2A in the cross-sectional displacement depicted. The acoustic wave consists essentially of only shear vibrations of atoms and therefore has essentially no vertical component of displacement above the surface of device. There is also surface displacement of atoms that is shear in the plane of the plate, as also depicted.

SHAPM device 210 is suitable for liquid level sensing, as the damping of SAW devices significantly reduced this capability, because in the case of SAW devices there is a vertical component of atom vibrations perpendicular to the surface of its piezoelectric crystal substrate, which is blocked by weight of the liquid. For the case of the SHAPM device 210 in FIG. 2A, a maximum displacement of piezoelectric substrate atoms takes place on the top and bottom surface of the piezoelectric crystal substrate 205. A continuous energy transfer between the top and bottom crystal surfaces of piezoelectric crystal substrate 205 allows the acoustic signals propagating between the electrodes of the input IDT 211 and the output IDT 201 to be influenced by environmental changes including mass loading, visco-elastic properties and electro-acoustic interactions taking place on the opposite surface of the piezoelectric crystal substrate 205. SHAPM device 210 has the advantage where the acoustic coupling of these two opposing surfaces makes this device particularly useful for level detection in harsh fluids, since one can isolate the metal electrodes of the IDTs 201, 211 from corrosive liquids by being on the side opposite that having the liquid.

Disclosed embodiments utilizing SHAPM devices such as SHAPM device 210 by virtue of having both IDTs 201, 202 on the same side of the substrate permits the SHAPM device to sense on the side opposite the IDTs 201, 202 thus solving the problem of electrode corrosion when level sensing of corrosive liquids without the need for a conventionally needed passivation layer. This embodiment as a result provide a better sensor solution from a reliability point of view by enabling unpassivated sensors, and reduced device complexity and possible performance degradation in the case of a conventional protective passivation layer for the sensor.

Figure 2B:
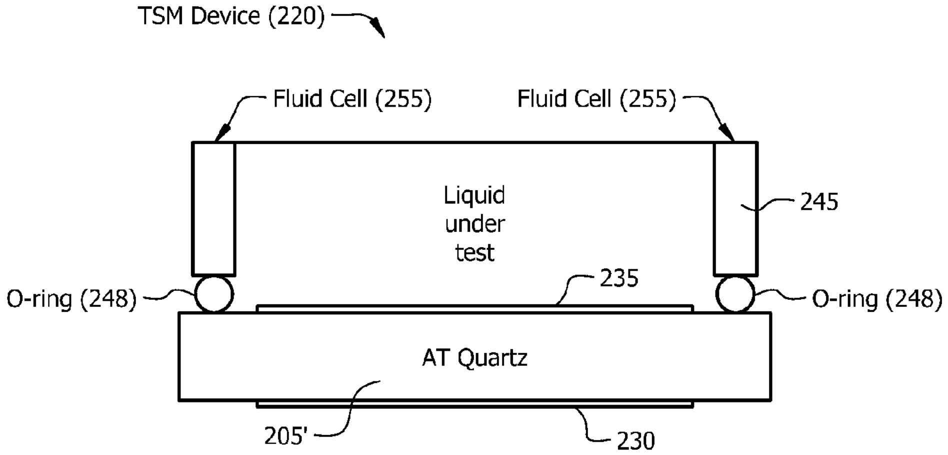

FIG. 2B depicts an example TSM device 220. TSM devices are a form of BAW device where thickness shear vibration is in the plane of crystal plate with maximum displacement occurring on the faces of the piezoelectric crystal substrate shown in FIG. 2B as an AT cut quartz substrate 205'. There are metal electrodes 230 and 235 on opposite faces (bottom and top) of the AT quartz substrate 205'. TSM device 220 includes the fluid cell shown 255 that comprises side walls 245 e.g., made of plastic material such as Poly(vinyl chloride) commonly referred to as PVC) on an O-ring (e.g., a fluoroelastomeric polymer material such as VITON™) 248 on the top surface of the piezoelectric crystal substrate 205' that is beyond and thus surrounds the metal electrode 235. The thickness shear acoustic vibration travels through the bulk of the AT cut quartz substrate 205' between the two electrodes 230/235. The thickness shear acoustic vibration has essentially no vertical component. The maximum atom displacement occurs on the upper and lower crystal face of the AT cut quartz substrate 205'. TSM device 220 is suitable for fluid sensing, but may have lower reliability in corrosive environments because one of the electrodes (electrode 235 in FIG. 2B) during operation is exposed to the sensing liquid. From such a reason noble metal electrodes such as platinum can be used for increased sensor reliability for TSM device 220.

Since SHAPM and TSM devices can measure a large range of acoustic viscosities, these devices can measure multiple interfaces between liquids, such as water and oil together in the same tank. Thus, as one can differentiate various liquid during their detection so that inexpensive liquid spectroscopy can be realized with BAW devices, which can be a significant added value particularly to plant and refinery operations, with respect to the known methods commercially available. This aspect is described below.

Figure 3A:
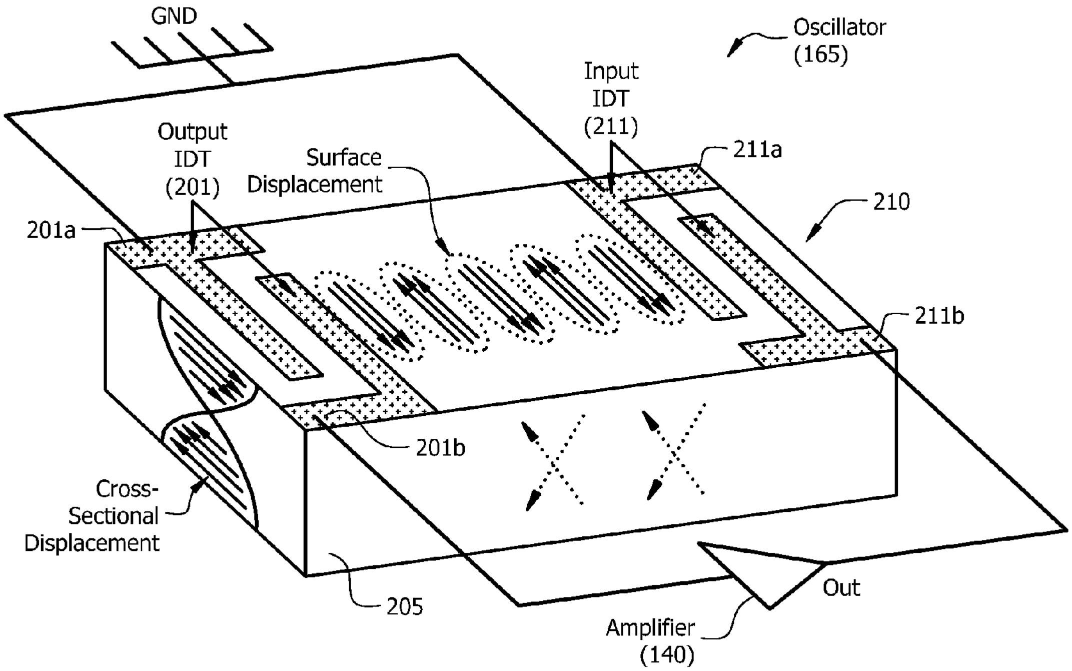
FIG. 3A depicts an example SHAPM-based electronic oscillator where the SHAPM device is connected across the feedback loop of an amplifier to provide positive feedback to form an electronic oscillator, according to an example embodiment.

Several example applications for disclosed BAW sensors are now described. A first application is the measurement of point level using the BAW device as a switch for a contact method. FIG. 3A depicts an example of electronic oscillator 165 including an amplifier 140 with the SHAPM device 210 described above relative to FIG. 2A in the positive feedback loop of the amplifier 140 (between the output of the amplifier 140 and its input) with one of the electrodes of the input IDT 211 connected to the output of the amplifier 140, and the one of the electrodes of the output IDT 201 connected to the input of the amplifier 140 to render the amplifier 140 together with the SHAPM device 210 the electronic oscillator 165 shown. The other electrodes of the output IDT 201 (201*a*) and input IDT 211 (211*a*) are connected together, and are shown coupled to a system ground (shown as GND). The resulting electronic oscillator 165 can measure at the output of the amplifier 140 the frequency shift due to fluid change (e.g., immersion in a fluid).

Figure 3B:
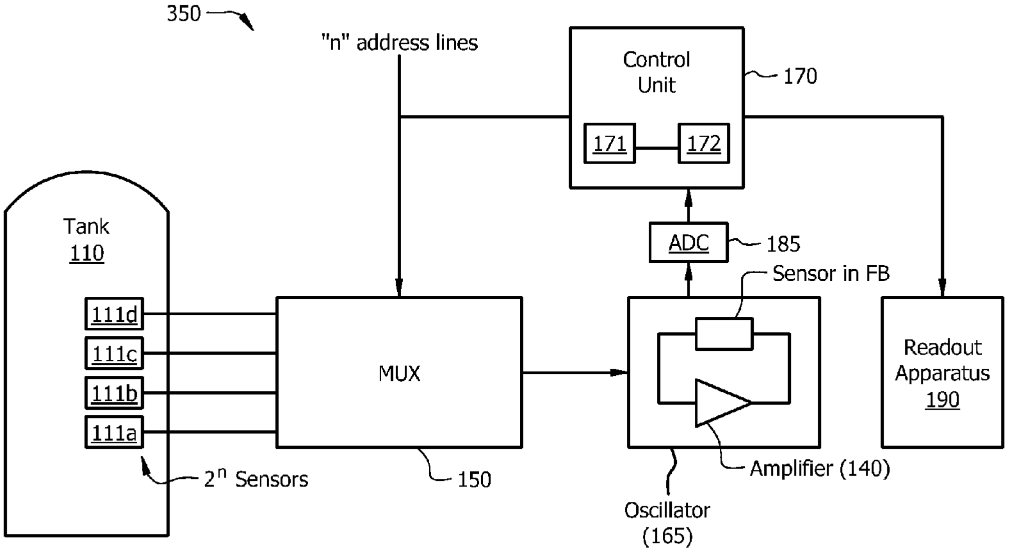
FIG. 3B is a block diagram depiction of a multi-sensor system for sensing at least one level parameter of at least one liquid in a tank having an oscillator based on a BAW sensor connected across a feedback loop of an amplifier, to which a multiplexer (MUX) based on unique digital addresses, provided by a control unit couples the respective BAW sensors in the sensor array one by one to the feedback loop of the amplifier, according to an example embodiment.

FIG. 3B shows a block diagram depiction of a multi-sensor (sensor array) system 350 having an amplifier 140, to which a MUX 150 couples one-by-one the respective BAW sensors 111*a-d* in the sensor array 111 within the tank 110 to the feedback loop of amplifier 140 to provide an electronic oscillator 165, according to an example embodiment. Each sensor 111*a-d* when its unique binary address (up to $2^n$ BAW sensors) is provided by the control unit 170 via "n" address lines to the MUX 150, becomes connected into the-feedback loop of the amplifier 140 which will determine the oscillation frequency of the resulting oscillator 165, which has its output coupled the control unit 170 by an ADC 185.

The oscillation frequency, and the oscillation frequency shift with respect to air (or other gas), carries information about the acoustic viscosity of the medium (e.g., liquid) in which the particular BAW sensor 111*a*-111*d* is immersed, is processed by processor 171 of the control unit 170 and is displayed by the readout apparatus 190 in terms of level and interface (s) information. The acoustic viscosity of the air can be important for this application, as any increase of the acoustic viscosity with respect to air will indicate that the particular sensor is immersed in a liquid, while any unchanged value with respect air, will indicate that the particular sensor is still "immersed" in air, as a generic state.

Point level detection can be provided by BAW sensors described above. As an example, referring to the two tank arrangement including mineral oil and air in each tank with different mineral oil levels shown in FIG. 3C and FIG. 3D, if one wants to control the liquid level in a tank 110 to be between two positions referred to herein as "overfilled" and "empty" as shown in FIGS. 3C and 3D, respectively, one can use two (or more) BAW sensors 301 and 302, where BAW sensor 301 is placed at a height considered to be in the "overfill" position, while the BAW sensor 302 is placed at a height considered to be the "empty" position.

Figure 3C:
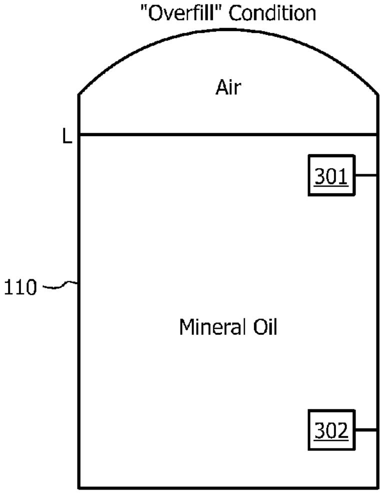
FIG. 3C and FIG. 3D each shows a tank arrangement including mineral oil and air with different mineral oil levels shown, according to an example embodiment.
Figure 3D:
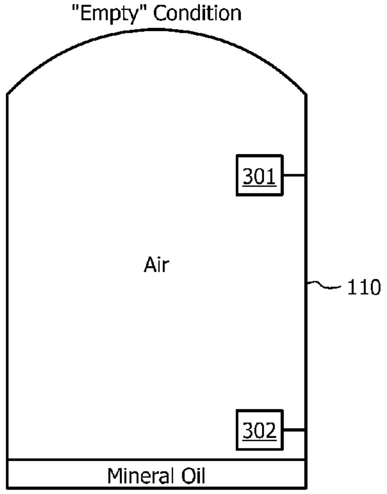

In the case of BAW sensors, in the "overfill" condition shown in FIG. 3C both BAW sensors 301 and 302 are immersed in mineral oil, and the acoustic viscosity measured by each BAW sensor 301, 302 is high. In the "empty" state, as shown in FIG. 3D both BAW sensors 301, 302 being exposed to air instead of mineral oil will indicate zero acoustic viscosity. In the "normal" state the upper BAW sensor 301 will be exposed to air and will thus indicate a zero acoustic viscosity, while the lower BAW sensor 302 will be exposed to mineral oil and the measured acoustic viscosity measured will be high, indicating a "normal" state in the tank. Although SAW devices can perform this point level detection function, SAW devices cannot perform the other liquid level applications described below.

Another example application is the measurement of quasi-continuous level and single interface by BAW devices in contact with a liquid. This measurement exploits the high sensitivity of the BAW sensors to the acoustic viscosity of liquids. To obtain level information, a plurality of disclosed BAW sensors are positioned along the vertical direction (height) of the tank, such as at a constant distance between them, and their position and binary address can be recorded by the system (e.g., see FIG. 1 and its description). In addition, the maximum liquid height to be detected can be a multiple number of the distance between two BAW sensors. The liquid level can be given by simple calculations after knowing the response of all of the BAW sensors, grouping their response in two groups, one group of BAW sensors having the same response specific to air, and the other group of BAW sensors specific to liquid. After counting the number of BAW sensors in each group, the liquid level can be calculated. For multiple liquids and interfaces, grouping the response data into more BAW sensor groups is possible.

Yet another application is the measurement of quasi-continuous level and multiple interfaces by BAW devices in contact with liquid state. BAW sensors are recognized to be suitable for this application as they show a good accuracy for acoustic viscosity detection, which helps discriminate air and different liquids by their acoustic viscosity. Considering for example, the range of the SHAPM sensors which is from zero to 4,000, and frequency shift sensitivity of 224 ppm per (acoustic viscosity)$^{1/2}$, the discrimination between multiple types of liquid in the same tank can be provided, by following the procedure as described above. More information regarding this quasi-continuous level and multiple interfaces application is provided in the Examples below.

EXAMPLES

Disclosed embodiments are further illustrated by the following specific Examples, which should not be construed as limiting the scope or content of this Disclosure in any way.

Example 1

Regarding point level detection, the sensitivity of point level detection by BAW sensors is provided by direct-contact acoustic viscosity measurement. As noted above, point level measurement can be rendered by BAW (e.g., SHAMP, TSM) devices. The reader can be an electronic oscillator circuit with the BAW sensor in the positive feedback loop, where frequency shift due to fluid change can be used to measure the level/interface (See FIG. 3A). The extracted parameter is acoustic viscosity=product of density ($g/cm^3$) and viscosity (cP). In this approach the acoustic viscosity of a liquid being much higher than the acoustic viscosity of air is utilized.

For Example, for Air @ 20° C.:

Air density=1.18 Kg/m3=1.18*1000 g/1000000 $cm^3$=1.18*$10^{-3}$ $g/cm^3$

Air viscosity=17.9 μPa*s=17.9*$10^{-3}$ mPa*s=17.9*$10^{-3}$ cP (dynamic viscosity) (1 cP=1 mPa·s=0.001 Pa·s)

Acoustic viscosity=1.18*$10^{-3}$ $g/cm^3$*17.9*$10^{-3}$ cP*cP=1.18*17.9*$10^{-6}$ ($g/cm^3$)*cP=21.12*$10^{-6}$ $g/cm^3$*cP A BAW device measuring such a value of acoustic viscosity will be associated to the sensor exposed to air.

Another Example for Lubricating Oil @20° C.

Oil density=920 $Kg/m^3$=0.92 $g/cm^3$

Oil viscosity=799×$10^{-3}$ Pa-s=799 cP (dynamic viscosity) Acoustic viscosity=735.08 ($g/cm^3$)*cP which is much higher than the acoustic viscosity of air.

A BAW sensor measuring such a value of acoustic velocity will be associated to a sensor immersed in oil. If the fluid density is known, then "pure" viscosity can be measured, but this is not necessary for point level measurement. The acoustic viscosity of oil measured by BAW sensors may be much higher than that of air.

Example of Water @20° C.

Water density=0.998 $g/cm^3$

Viscosity=2.18*$10^{-3}$ Pa*s=2.18 cP

Acoustic viscosity=2.175 ($g/cm^3$)cP

The discrimination between air, oil and water is simple and accurate when measuring the acoustic viscosity using disclosed BAW sensors. Reliable point level measurement by BAW sensors can be thus made. For example, a VISMART™ SHAPM sensor from Vectron International can measure viscosity from zero (air) to 10,000 cP (different mineral oils), or even 100,000 cP for different types of printing inks.

Example 2

This Example is for point level measurement by BAW sensors in direct-contact with fluid to monitored using "overfill" and "empty" conditions. (See FIGS. 3C and 3D). In the case of lubricating oil in the tank 110 in the "overfill" condition, the two BAW sensors, 301 and 302 will indicate a high value of acoustic viscosity, as noted above. An audible alarm or other indication (e.g. flashing light) can be triggered responsive to sensing an overfill condition.

In the case of lubricating oil in the tank being in the "empty" condition, the two BAW sensors, 301 and 302 will indicate a low value of the acoustic viscosity, as noted above. An alarm or other indication is to be triggered can be triggered by this "empty" condition.

In the case of lubricating in the tank being in the normal level stage, the BAW sensor 301 will indicate a low value of acoustic viscosity, while the BAW sensor 302 will indicate a high value of acoustic viscosity. An indication of normal level stage will be shown by can be shown by an electronic reader.

Example 3

Principle of quasi-continuous level measurement: A plurality of BAW sensors are placed on the vertical wall of the tank with equal distance between two consecutive BAW sensors and between the last sensor and the bottom of the tank, as well as from the maximum measurable height to the first sensor. Each BAW sensor has a defined binary address and thus a known recorded (stored in memory) vertical position in the tank.

Figure 4A:
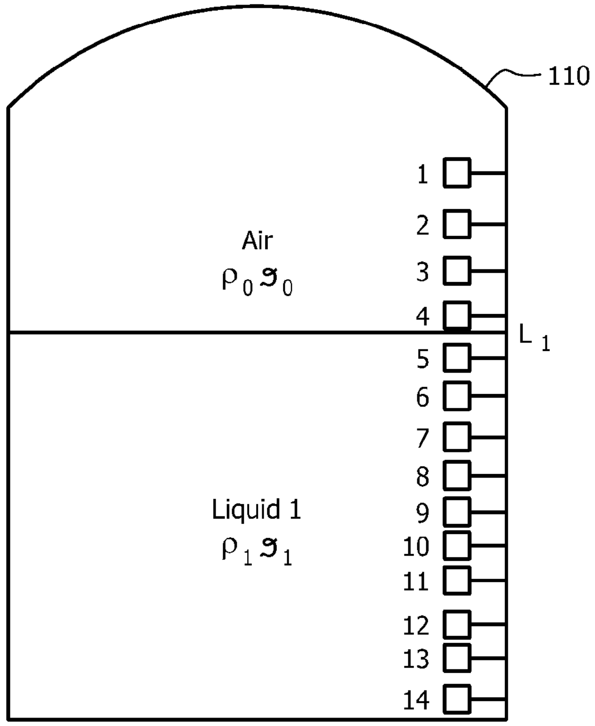
FIG. 4A shows a vertical stack of fourteen (14) disclosed BAW devices in a tank placed vertically on the vertical wall of the tank partially filled with liquid, according to an example embodiment.

FIG. 4A shows a vertical stack of 14 discloses BAW sensors in a tank 110 partially filled with a liquid shown as Liquid 1. A higher number of BAW sensors will increase the accuracy in level determination. The dimension of each BAW sensor may limit the level accuracy, ultimately. Thus, the height that can be monitored is H=(n+1)*d=15d (in this Example), where "n" is the number of BAW sensors and "d" is distance between two consecutive BAW sensors, as shown in the right side figure.

After the system of BAW sensors is powered on, they will respond according to their type, providing the acoustic viscosity in the case of BAW. In this example, the BAW sensors 1-4 will indicate the acoustic viscosity of air, while the BAW sensors 5-14 will indicate the acoustic viscosity ($\rho_1$*$\vartheta_1$) of the liquid. The processor 171 within the control unit 170 will thus "know" that all the similar readings mean that those BAW sensor are exposed to either air or immersed in the liquid.

The processor 171 of control unit 170 will provide the level (position of interface $I_1$ between liquid and air) by counting the BAW sensor with minimum acoustic viscosity (almost zero) and doing the calculation described below (according to FIG. 4A:

$$\text{Level}=H-4*d=15d-4d=11d.$$

The accuracy of quasi-continuous level measurement is equal with the distance "d" between two consecutive BAW sensors.

It is noted that if there is foam at the interface, this foam can be detected by the value of the acoustic viscosity of the BAW sensor "seeing" that foam. The acoustic viscosity of the foam should be an intermediate value between that of the air and the acoustic viscosity of the bulk liquid.

Example 4

Figure 4B:
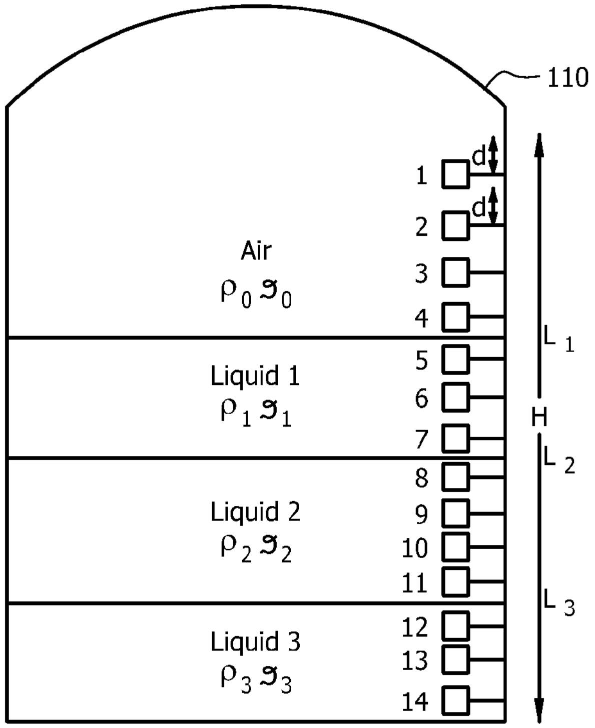
FIG. 4B shows a vertical stack of fourteen (14) disclosed BAW devices in a tank placed vertically on the vertical wall of the tank having three (3) different immiscible liquids therein, according to an example embodiment.

Example of quasi-continuous level and multiple interfaces measurement by BAW devices in direct contact with liquid: FIG. 4B shows a plurality of BAW sensors placed vertically on the vertical wall of a tank 110 having a plurality of different immiscible liquids therein. Typically, there is an equal distance between two consecutive BAW sensors and between the last BAW sensor and the bottom of the tank, such as shown in FIG. 4B. Each BAW sensor has a unique binary address and a relative position in the tank recorded in the memory 172 of the control unit 170. For example, as per FIG. 4A, for a total number of BAW sensors smaller or equal to 16, sensor 4 can have the binary address 0100 and it is the fourth sensor from the top, at the position H−4*d, where H is the total length under control, which is H=15d. For level and interface assessment, the calculations of numerical values will always start from top to the bottom, the position of the sensors being well known.

Although 14 sensors are shown in FIGS. 4A and 4B, a higher number of BAW sensors will provide an increased accuracy in level determination. The dimension of each sensor may limit the level accuracy, ultimately. Thus, the height that can be monitored is H=(n+1)*d, where "n" is the number of sensors and "d" is distance between two consecutive sensors, and from the top to the first sensor, and from the $14^{th}$ BAW sensor and the bottom of the tank as shown in the right side figure.

After the system of sensors is powered on, each of them will provide the local acoustic viscosity. In this example relating to FIG. 4B, BAW sensors 1-4 will indicate the acoustic viscosity of air, the BAW sensors 5-7 will indicate the acoustic viscosity of liquid 1 $(\rho_1 * \vartheta_1)$, the BAW sensors 8-11 will indicate the acoustic viscosity of the liquid 2 $(\rho_2 * \vartheta_2)$, and the BAW sensors 12-14 will indicate the acoustic viscosity of the liquid 3 $(\rho_3 * \vartheta_3)$.

The processor 171 will thus know that all the similar readings mean that those sensors are exposed to either air or immersed in a certain liquid. The processor 171 will provide the level (position of interface $I_1$ between liquid and air) by counting the number of BAW sensors with minimum acoustic viscosity (almost zero), (in our case that number is equal to 4), and doing the calculation below:

$$\text{Level}=H-4d=15d-4d=11d$$

The interface $I_2$ can be identified looking at the acoustic viscosities of the next group of BAW sensors with similar acoustic viscosity, higher than zero (in FIG. 4B BAW sensors 5, 6, 7). After counting them, the position of the interface $I_2$ is given:

$$I_2=H-4d-3d=15d-7d=8d.$$

Similarly, the position of the interface $I_3$ will be given as:

$$I_3=H-4d-3d-4d=H-11d=15d-11d=4d$$

The error of this method is equal to +/−d, the distance between two consecutive BAW sensors.

It is noted if there is foam at one of the interfaces $I_1$, $I_2$, or $I_3$ from above, the foam would have an acoustic viscosity which should be an intermediate value between the value of acoustic viscosity of air and that of the upper and lower surrounding liquids. Another algorithm may be used for subtracting the volume of foam) from the total volume of fluid, which can be derived from level and interfaces positions. For example, if the foam is covering BAW sensors 3 and 4 in FIG. 4A, their acoustic viscosity will be not much higher than of air, but much lower than the acoustic viscosity of the BAW sensors 5-14 (that are exposed to the liquid). Thus, one may determine the foam height by the distance between these two BAW sensors.

While various disclosed embodiments have been described above, it should be understood that they have been presented by way of example only, and not limitation. Numerous changes to the subject matter disclosed herein can be made in accordance with this Disclosure without departing from the spirit or scope of this Disclosure. In addition, while a particular feature may have been disclosed with respect to only one of several implementations, such feature may be combined with one or more other features of the other implementations as may be desired and advantageous for any given or particular application.

The invention claimed is:

1. A method for sensing at least one level parameter of at least one liquid in a tank, comprising:

providing at least one bulk acoustic wave (BAW) sensor positioned inside said tank, wherein electrodes of said at least one BAW sensor are at least switchably connected to a positive feedback loop across an amplifier to provide an electronic oscillator, wherein said at least one BAW sensor each have a unique digital address stored in a memory associated with a control unit that provides sensor select signals to a multiplexer (MUX), said MUX individually interrogating said plurality of BAW sensors;

determining a frequency shift from an output of said electronic oscillator by utilizing a calibration curve relating a measured change in resonant frequency for said electronic oscillator to said liquid, wherein said output of said electronic oscillator is different when said at least one BAW sensor contacts said liquid as compared to when said at least one BAW sensor contacts air, and using said unique digital address and a distance between consecutive ones of said at least one BAW sensor in an algorithm for determining said level parameter from said change in resonant frequency.

2. The method of claim 1, wherein said at least one BAW sensor comprises a shear horizontal acoustic plate mode (SHAPM) device.

3. The method of claim 1, wherein said at least one BAW sensor are stacked vertically along a vertical wall of said tank, said at least one BAW sensor each for obtaining said change in said resonant frequency at different positions along a height of said tank.

4. The method of claim 3, wherein said level parameter comprises a point level.

5. The method of claim 3, wherein said liquid forms an interface with said air above, further comprising determining a presence of foam at said interface from a plurality of said changes in said resonant frequency obtained using said at least one BAW sensor.

6. The method of claim 3, wherein said liquid comprises a plurality of immiscible liquids, and wherein said determining said level parameter comprises determining a quasi-continuous level and a position of one or more liquid interfaces.

7. The method of claim 3, wherein a vertical spacing between said at least one BAW sensor is a constant.

8. A system for sensing at least one level parameter of at least one liquid in a tank, comprising:

at least one bulk acoustic wave (BAW) sensor positioned inside said tank, wherein electrodes of said BAW sensor are at least switchably connected to a positive feedback loop across an amplifier to provide an electronic oscillator, wherein said at least one BAW sensor each have a unique digital address stored in a memory associated with a control unit that provides sensor select signals to a multiplexer (MUX), said MUX individually interrogating said at least one BAW sensor, and a control unit including a processor and memory coupled to an output of said electronic oscillator, said control unit determining a frequency shift from said output of said electronic oscillator by utilizing a calibration curve stored in said memory relating a measured change in resonant frequency for said electronic oscillator to said liquid, wherein said output of said electronic oscillator is different when said at least one BAW sensor contacts said liquid as compared to when said at least one BAW sensor contacts air, wherein said control unit uses said unique digital address and a distance between consecutive ones of said at least one BAW sensor in an algorithm for determining said level parameter from said change in resonant frequency.

9. The system of claim 8, wherein said at least one BAW sensor comprises a shear horizontal acoustic plate mode (SHAPM) device.

10. The system of claim 8, wherein said at least one BAW sensor are stacked vertically along a vertical wall of said tank, said at least one BAW sensor each for obtaining said change in said resonant frequency at different positions along a height of said tank.

11. The system of claim 10, wherein said control unit is coupled to said MUX by a plurality of address lines for providing a selected one of said unique digital address at any given time to said MUX, and wherein said selected one of said digital unique address corresponds to a digital address of a selected one of said at least one BAW sensor which when selected becomes connected across said positive feedback loop of said amplifier.

12. The system of claim 10, wherein said liquid forms an interface with said air above, wherein said control unit determines a presence of foam at said interface from a plurality of said frequency shift measurements obtained using said at least one BAW sensor.

13. The system of claim 8, wherein said liquid comprises a plurality of immiscible liquids, and wherein said control unit determining said level parameter determines a quasi-continuous level and a position of one or more liquid interfaces.

* * * * *